US011865139B2

(12) United States Patent
Kramer et al.

(10) Patent No.: US 11,865,139 B2
(45) Date of Patent: *Jan. 9, 2024

(54) METHOD OF TREATING MIGRAINES AND HEADACHES

(71) Applicant: ThermoLife International, LLC, Signal Hill, CA (US)

(72) Inventors: Ronald Kramer, Signal Hill, CA (US); Alexandros Nikolaidis, Nea Kallikratia (GR)

(73) Assignee: THERMOLIFE INTERNATIONAL, LLC, Signal Hill, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/835,805

(22) Filed: Jun. 8, 2022

(65) Prior Publication Data
US 2022/0296638 A1 Sep. 22, 2022

Related U.S. Application Data

(63) Continuation-in-part of application No. 17/670,383, filed on Feb. 11, 2022, which is a continuation of application No. PCT/US2022/016231, filed on Feb. 11, 2022, and a continuation-in-part of application No. 17/525,841, filed on Nov. 12, 2021.

(60) Provisional application No. 63/232,852, filed on Aug. 13, 2021, provisional application No. 63/180,039, filed on Apr. 26, 2021, provisional application No. 63/148,523, filed on Feb. 11, 2021, provisional application No. 63/148,517, filed on Feb. 11, 2021, provisional application No. 63/113,114, filed on Nov. 12, 2020.

(51) Int. Cl.
| | | |
|---|---|---|
| A61K 33/06 | (2006.01) | |
| A61P 25/06 | (2006.01) | |
| A61K 33/30 | (2006.01) | |
| A61K 33/24 | (2019.01) | |
| A61K 31/375 | (2006.01) | |
| A61K 31/194 | (2006.01) | |
| A61K 9/00 | (2006.01) | |
| A61K 33/26 | (2006.01) | |

(52) U.S. Cl.
CPC ............ *A61K 33/06* (2013.01); *A61K 9/0053* (2013.01); *A61K 31/194* (2013.01); *A61K 31/375* (2013.01); *A61K 33/24* (2013.01); *A61K 33/26* (2013.01); *A61K 33/30* (2013.01); *A61P 25/06* (2018.01)

(58) Field of Classification Search
None
See application file for complete search history.

(56) References Cited

U.S. PATENT DOCUMENTS

| | | |
|---|---|---|
| 1,916,983 A | 7/1933 | McKee |
| 2,176,144 A | 10/1939 | Moskowitz |
| 2,553,533 A | 5/1951 | Komarik |
| 3,230,036 A | 1/1966 | Kappelmann |
| 3,552,978 A | 1/1971 | Petrus |
| 3,886,040 A | 5/1975 | Chibata |
| 3,997,659 A | 12/1976 | Knohl |
| 4,146,611 A | 3/1979 | Ondetti |
| 4,291,015 A | 9/1981 | Keith |
| 4,379,177 A | 4/1983 | McCoy |
| 4,687,782 A | 8/1987 | Brantman |
| 4,743,614 A | 5/1988 | Terano |
| 4,749,402 A | 6/1988 | Garrett |
| 4,871,550 A | 10/1989 | Millman |
| 4,976,960 A | 12/1990 | Grossman |
| 4,996,067 A | 2/1991 | Kobayashi |
| 5,026,071 A | 6/1991 | Miraglia, Jr. |
| 5,026,721 A | 6/1991 | Dudrick |
| 5,242,697 A | 9/1993 | Luca |
| 5,485,827 A | 1/1996 | Zapol |
| 5,500,436 A | 3/1996 | Schonafinger |
| 5,543,430 A | 8/1996 | Kaesemeyer |
| 5,576,351 A | 11/1996 | Yoshimura |
| 5,631,031 A | 5/1997 | Meade |
| 5,679,704 A | 10/1997 | Schonafinger |
| 5,767,160 A | 6/1998 | Kaesemeyer |

(Continued)

FOREIGN PATENT DOCUMENTS

| | | |
|---|---|---|
| CN | 1056225 | 11/1991 |
| CN | 1049824 | 3/2000 |

(Continued)

OTHER PUBLICATIONS

Gonzalez, "Migraines are Correlated with Higher Levels of Nitrate-, Nitrite-, and Nitric Oxide-Reducing Oral Microbes in the American Gut Project Cohort". mSystems. Oct. 18, 2016;1(5):e00105-16. doi: 10.1128/mSystems.00105-16. Erratum in: mSystems. (Year: 2016).*
Glyceryl trinitrate—leaflet print—Patient UK, available at http://www.patient.co.uk/printer.asp?dock=30003883, 2009.
Heart attack—Nitrates & vasodilators—Revolution Health, available at http://www.revolutionhealth.com/conditions/ heart/herat-attack/medication-types/nitrates-vasodilators/ 2011.
"Isosorbide dinitrate—leaflet print—Patient UK," available at http://www.patient.co.uk/printer.asp?doc= 30003884, 2011.
"Isosorbide mononitrate-leaflet print—Patient UK," available at http://www.patient.co.uk/printer.asp?doc=30003885, 2008.

(Continued)

*Primary Examiner* — Robert T. Crow
*Assistant Examiner* — John P Nguyen
(74) *Attorney, Agent, or Firm* — Booth Udall Fuller, PLC; Pacer K. Udall

(57) ABSTRACT

The disclosure is directed to compositions and methods of treating or preventing headaches, including migraines. The compositions comprise a nitrate anion source, an elemental metal (uncharged), and an acid. The compositions are preferably administered orally. In some aspects, the product of a reaction of the nitrate anion source, the elemental metal (uncharged), and the acid are administered to the subject via inhalation.

26 Claims, 4 Drawing Sheets

(56) References Cited

U.S. PATENT DOCUMENTS

| | | |
|---|---|---|
| 5,904,924 A | 5/1999 | Gaynor |
| 5,965,596 A | 10/1999 | Harris |
| 6,063,432 A | 5/2000 | Maxwell |
| 6,136,339 A | 10/2000 | Gardiner |
| 6,159,485 A | 12/2000 | Yu |
| 6,172,098 B1 | 1/2001 | Harris |
| 6,277,884 B1 | 8/2001 | De Tejada |
| 6,337,349 B2 | 1/2002 | Scafetta |
| 6,451,341 B1 | 9/2002 | Slaga |
| 6,562,869 B1 | 5/2003 | Hamilton |
| 6,608,109 B2 | 8/2003 | Allen |
| 6,784,209 B1 | 8/2004 | Gardiner |
| 7,235,237 B2 | 6/2007 | Loscalzo |
| 7,777,014 B2 | 8/2010 | Cattaruzza |
| 7,777,074 B2 | 8/2010 | Kramer |
| 7,799,782 B2 | 9/2010 | Munson |
| 8,034,836 B2 | 10/2011 | Kramer |
| 8,048,921 B2 | 11/2011 | Kramer |
| 8,178,572 B2 | 5/2012 | Kramer |
| 8,183,288 B2 | 5/2012 | Kramer |
| 8,455,531 B2 | 6/2013 | Kramer |
| 8,466,187 B2 | 6/2013 | Kramer |
| 8,569,368 B2 | 10/2013 | Kramer |
| 8,569,369 B2 | 10/2013 | Kramer |
| 8,703,719 B1 | 4/2014 | Abraham |
| 8,852,660 B2 | 10/2014 | Miljkovic |
| 8,952,045 B1 | 2/2015 | Kramer |
| 8,952,046 B1 | 2/2015 | Kramer |
| 8,957,100 B1 | 2/2015 | Kramer |
| 8,957,101 B1 | 2/2015 | Kramer |
| 9,180,140 B2 | 11/2015 | Lundberg |
| RE46,372 E | 4/2017 | Miller |
| 10,646,508 B1 | 5/2020 | Kramer |
| 10,736,916 B1 | 8/2020 | Kramer |
| 2001/0002269 A1 | 5/2001 | Zhao |
| 2001/0048952 A1 | 12/2001 | Siskind |
| 2001/0055617 A1 | 12/2001 | Mattern |
| 2001/0056069 A1 | 12/2001 | Klaus |
| 2002/0006532 A1 | 1/2002 | Robin |
| 2002/0065323 A1 | 5/2002 | Crooks |
| 2002/0119933 A1 | 8/2002 | Butler |
| 2002/0147156 A1 | 10/2002 | Petit |
| 2003/0012744 A1 | 1/2003 | Pedersen |
| 2003/0014238 A1 | 1/2003 | Xun |
| 2003/0091615 A1 | 5/2003 | Craig |
| 2003/0097401 A1 | 5/2003 | Bauman |
| 2003/0119888 A1 | 6/2003 | Allen |
| 2003/0139354 A1 | 7/2003 | Buccholz |
| 2004/0006140 A1 | 1/2004 | Kaesemeyer |
| 2004/0048870 A1* | 3/2004 | Amir ............ A61K 31/525 |
| | | 514/250 |
| 2004/0057926 A1 | 3/2004 | Ochoa |
| 2004/0058011 A1 | 3/2004 | Petersson |
| 2004/0087518 A1 | 5/2004 | Verlaan |
| 2004/0097401 A1 | 5/2004 | Datta |
| 2004/0126366 A1 | 7/2004 | Kaddurah-Daouk |
| 2004/0224868 A1 | 11/2004 | Meyerhoff |
| 2004/0242682 A1 | 12/2004 | Kaesemeyer |
| 2005/0043274 A1 | 2/2005 | Murad |
| 2005/0053673 A1 | 3/2005 | Netke |
| 2005/0171194 A1 | 8/2005 | Yu |
| 2005/0196474 A1 | 9/2005 | Anno |
| 2005/0256192 A1 | 11/2005 | Gardiner |
| 2005/0261257 A1 | 11/2005 | Vermeer |
| 2005/0287210 A1 | 12/2005 | Ron |
| 2005/0288372 A1 | 12/2005 | Ron |
| 2005/0288373 A1 | 12/2005 | Ron |
| 2006/0014238 A1 | 1/2006 | Gholap |
| 2006/0018281 A1 | 1/2006 | Sadot |
| 2006/0029668 A1 | 2/2006 | Ron |
| 2006/0063827 A1 | 3/2006 | Yu |
| 2006/0116328 A1 | 6/2006 | Babizhayev |
| 2006/0142382 A1 | 6/2006 | Morimoto |
| 2006/0182815 A1 | 8/2006 | Gladwin |
| 2006/0198899 A1 | 9/2006 | Gardiner |
| 2006/0241181 A1 | 10/2006 | Pola |
| 2006/0275909 A1 | 12/2006 | Spitzer |
| 2007/0037880 A1* | 2/2007 | Mailland ............ A61P 31/00 |
| | | 514/474 |
| 2007/0105817 A1 | 5/2007 | Page |
| 2007/0141174 A1 | 6/2007 | Cornett |
| 2007/0154569 A1 | 7/2007 | Gladwin |
| 2008/0004218 A1 | 1/2008 | Quay |
| 2008/0026075 A1 | 1/2008 | Kondo |
| 2008/0038410 A1 | 2/2008 | Giordano |
| 2008/0138448 A1 | 6/2008 | Heuer |
| 2008/0214649 A1 | 9/2008 | Yu |
| 2008/0233186 A1 | 9/2008 | Romero |
| 2008/0268095 A1 | 10/2008 | Herzog |
| 2009/0076110 A1 | 3/2009 | Kramer |
| 2009/0137670 A1 | 5/2009 | Kramer |
| 2009/0280199 A1 | 11/2009 | Russell |
| 2009/0306208 A1 | 12/2009 | Shimada |
| 2010/0004335 A1 | 1/2010 | Kagami |
| 2010/0047344 A1 | 2/2010 | Lundberg |
| 2010/0092441 A1 | 4/2010 | Lundberg |
| 2010/0172890 A1 | 7/2010 | Gilad |
| 2011/0064712 A1 | 3/2011 | Amato |
| 2011/0123654 A1 | 5/2011 | Jaeger |
| 2012/0220643 A1 | 8/2012 | Kramer |
| 2013/0071494 A1 | 3/2013 | Bryan |
| 2013/0101704 A1 | 4/2013 | Meehan |
| 2015/0246066 A1 | 9/2015 | Nelson |
| 2017/0042935 A1* | 2/2017 | Sakamoto ............ A61P 1/04 |
| 2017/0303582 A1 | 10/2017 | Lu |
| 2018/0133247 A1 | 5/2018 | Green |
| 2020/0222449 A1 | 7/2020 | Nikolaidis |
| 2021/0220422 A1 | 7/2021 | Parker |

FOREIGN PATENT DOCUMENTS

| | | |
|---|---|---|
| CN | 1631539 | 6/2005 |
| CN | 20041009958 | 6/2005 |
| EP | 797992 A2 | 1/1997 |
| EP | 1336602 | 8/2003 |
| EP | 1429829 B1 | 11/2013 |
| EP | 2896302 | 7/2015 |
| GB | 1089084 A | 11/1967 |
| GB | 2008578 A | 6/1979 |
| GB | 2052976 A | 2/1981 |
| GB | 2354441 | 3/2001 |
| KR | 20110015141 A | 2/2011 |
| WO | 9843499 | 10/1998 |
| WO | 0040217 | 7/2000 |
| WO | 0195897 | 12/2001 |
| WO | 03063789 A2 | 8/2003 |
| WO | 2005062713 | 7/2005 |
| WO | 2005115175 | 12/2005 |
| WO | 2005115175 A1 | 12/2005 |
| WO | 2006025286 | 3/2006 |
| WO | 2006124161 | 11/2006 |
| WO | 2007000985 | 1/2007 |
| WO | 2007066642 | 6/2007 |
| WO | 2007093808 | 8/2007 |
| WO | 2008009615 A1 | 1/2008 |
| WO | 2008043855 | 4/2008 |
| WO | 2008105730 | 9/2008 |
| WO | 2008105731 | 9/2008 |
| WO | 2020160509 A1 | 8/2020 |
| WO | 2020214841 A1 | 10/2020 |
| WO | 2021188163 | 9/2021 |

OTHER PUBLICATIONS

"Dietary Nitrate and Nitrite to Increase Nitric Oxide in Patients with Coronary Artery Disease," Clinical Trial available at http://clinicaltrials.gov/ct2/show/NCT00069654, 2010.

"Dymatize Nutritional Supplements, Whey Protein, Bodybuilding & Weight Products", 2013 Dymatize Enterprises LLC, Xpand 2x 36 Serving, http://www.dymatize.com/products/nitric-oxide/detail/1166/xpand-2x-36-serving, 2013.

(56) References Cited

OTHER PUBLICATIONS

"Heart attack—Nitrates & vasodilators—Revolution health," available at http://www.revolutionhealth.com/conditions/heart/heart-attack/medication-types/nitrates-vasodilators, 2011.
"Nitrates and nitrites (PIM G016)," available at http://www.inchem.org/documents/pims/chemical/pimg016.htm, 2011.
"Nitrates and Nitrites", TEACH Chemical Summary, U.S. EPA, Toxicity and Exposure Assessment for Children's Health, published by the U.S. Environmental Protection Agency on May 22, 2007 (Year: 2007).
"Xpand 2x by Dymatize at Bodybuilding.com—Lowest Price on Xpand 2x!", Advertisement, 2012 BodyBuilding.com, LLC., http://www.bodybuilding.com/store/dymatize/xpand-2x.html, Jun. 8, 2013.
21 C.F.R. (I)(B) §§ 172.160 and 172.170, revised Apr. 1, 2018 (Year: 2018).
A Butler, et al., Medieval Chinese Medicine: The Dunhuang Medical Manuscripts (Chapter 16: A treatment for carenovascular dysfunction in a Dunhuang medical manuscript), Routledge (2005).
Abd El-Gawad et al. AAPS PharmaSciTech, 2017, 18(5):1795-1809.
Abou-Mohamed et al. "Role of L-Arginine in the Vascular Actions and Development of Tolerance to Nitroglycerin", British Journal of Pharmacology (2000) 130, 211-218.
Ahtee et al."Taurine Biological Actions and Clinical Perspectives," J. Nutr. 116:2555-2556 (1986).
Amidon, G. L. et al., "Intestinal Absoption of Amino Acid Derivatives: Structural Requirements for Membrane Hydrolysis.", Journal of Pharmaceutical Sciences., (1983), vol. 72, No. 8, pp. 943-944, XP055127041.
Amino Thrust dietary supplement, 2007.
Anders et al. "Aminoacylases", 1994, Advances in Pharmacology, vol. 27, pp. 431-448. (Year: 1994).
Anderson, K. "Nitrate and Nitrite in Human Nutrition" The Graduate College in the University of Nebraska, Lincoln, Nebraska, 1982.
Aniya et al., "Evaluation of Nitric Oxide Formation from Nitrates in Pig Coronary Arteries," Jpn. J. Pharmacol. 71:101-107 (1996).
Archer, Evidence that ingested nitrate and nitrite are beneficial to health, Journal of food protection, vol. 65, No. 5, pp. 872-875, 2002.
Arenas et al., Muscle & Nerve, 1991, 14:598-604.
Arnold Iron CRE3, 2007.
Artioli et al. "Role of beta-Alanine Supplementation on Muscle Carnosine and Exercise Performance" Med. Sci. Sprots Exerc, Jun. 2010, vol. 42, No. 6pp. 1162-1173.
Atanasova, Plant Siol Environ, 2008, 54(2):66-71.
ATSDR Case Studies in Environmental Medicine Nitrate/Nitrite Toxicity published by the U.S. Department of Health and Human Services on Dec. 5, 2013. ATSDR Case Studies in Environmental Medicine Nitrate/Nitrite Toxicity.
Avraham et al., "Tyrosine improves appetite cognition and exercise tolerance in activity anorexia," Medicine & Science in Sports & Exercise, 33(12): 2104-2110, 2001.
B. C. Challis, Nutrition and nitrosamine formation, Proceeds of the Nutrition Society, vol. 44, pp. 95-100 (1985).
B. Spiegelhalder, et al., Influence of Dietary Nitrate on Nitrate Content of Human Saliva: Possible Relevance of N-Nitroso Compounds, Fd. Cosmet. Toxicol., vol. 14, pp. 545-548 (1976).
B. Sridhar, et al, "Bis (beta-alanine) Hydrogen Nitrate", Acta Crystallographica Section, 2001, pp. 1004-1006vol. 57.
Bahadur et al., "Crystal and molecular stucture of DL-aspartic acid nitrate monohydrate," Z. Kristallogr. 210: 276-278, 1995.
Bailey et al. "Dietary nitrate supplementation reduces the O2 cost of low-intensity exercise and enhances tolerance to high-intensity exercise in humans", J. Appl. Physiol., 2009, vol. 107, pp. 1144-1155. (Year: 2009).
Baran, "Crystal structure, phase transitions and vibrational spectra of bis(betaine) nitrate," Journal of Molecular Structure, 372: 131-144, 1995.
Barger, G. (1914) The Simpler Natural Bases. In R.H.A. Plimmer & F.G. Hopkins (Eds.) Monographs on Biochemistry (pp. 157-163) Longmans, Green & Co., London.

Barron JT and Parillo JE, "Production of lactic acid and energy metabolism in vascular smooth muscle: effect of dichloroacetate." Am J Physiol. Feb. 1995;268(2 Pt 2):H713-9.
Basheva et al."Role of Betaine as Foam Booster in the Presence of Silicone Oil Drops," Langmuir 16:1000-1013 (2000).
Bauer et al., "Vascular and Hemodynamic Differences between Organic Nitrates and Nitrites," Journal of Pharmacology and Experimental Therapeutics 280:326-331 (1997).
Bauer et al."Photochemical Generation of Nitric Oxide from Nitro-containing Compounds: Possible Relation to Vascular Photorelaxation Phenomena," Life Science 54(1):PL1-PL4 (1994).
BeetVO2Max—max Nitric Oxide Booster, Amazon.com, 2006.
Beghetti et al."Nitric oxide precursors and congenital cardiac surgery: A randomized controlled trial of oral citrulline. Definition of pulmonary hypertension in Fontan circulation?" J Thorac Cardioasc Surg 132(6):1501-1502 (2006).
Bendahan et al., "Citrulline/malate promotes aerobic energy production in human exercising muscle," Br. J. Sports Med., 36: 282-289, 2002.
Benjamin, Nigel, Nitrates in the Human Diet—good or bad?, Ann. Zootech. vol. 49, pp. 207-216 (2000).
Berge et al., Journal of Pharmarceutical Science, 66(1):1-19, 1977.
Betancourt product: Betancourt Ripped Juice EX2, 2006.
Beverly International advertisement in Dec. 1987 edition of Muscle & Fitness.
Blodgett et al. "Incidence of Hematologic Disease in Patients with Carpal Tunnel Syndrome" JAMA, 1962, 182(7), pp. 814-815.
Bloomer et al., "Comparison of pre-workout nitric oxide stimulating dietary supplements on skeletal muscle oxygen saturation, blood nitrate/nitrite, lipid peroxidation, and upper body exercise performance in resistance trained men", Journal of the International Society of Sports Nutrition 2010, 7:16, http://www.jissn.com/content/7/1/16.
Bloomer et al."Glycine propionyl-L-carnitine increases plasma nitrate/nitrite in resistance trained men," Journal of the International Society of Sports Nutrition 4(22):1-6 (2007).
Boger, "The Pharmacodynamics of L-Arginine," J. Nutr. 137: 1650S-1655S (2007).
Boguslavskiy. Effect of nitric oxide on the efficiency of oxygen usage by a working skeletal muscle under fatigue, Fiziol. Zhum., vol. 51, No. 1, pp. 33-42 (2005) & Certified Translation.
Borison et al., "Brain 2-phenylethylamine as a major mediator for the central actions of amphetamine and methylphenidate," Life Sci., 17: 1331-1344, Nov. 1975.
Bover-Cid et al., "Biogeneic Amine Accumulation in Ripened Sausages Affected by the Addition of Sodium Sulphite", Meat Science 59 (2001) 391-396, Mar. 20, 2001.
Bryan, N., "Food, Nutrition and the Nitric Oxide Pathway: Biochemistry and Bioactivity" 2010, pp. 59-63.
BSN Volumaize Aretic Blast, on line, sale product, 2014.
Burtscher. The Proonged Intake of L-Arginine-L-Aspartate Reduces Blood Lactate Accumulation and Oxygen Consumption During Submaximal Exercise, Journal of Sports Science and Medicine, vol. 4, pp. 314-322 (2005).
C. Oldreive, et al., The Mechanisms for Nitration and Nitrotyrosine Formation in vitro and in vivo: Impact of D;et, Free Rad. Res., vol. 35, pp. 215-231 (2001).
CAS Registry No. 89695-59-0 (1984).
Cavassa et al. WO98/43499.
CFIndustries, "Material Safety Data Sheet for Urea Ammonium Nitrate Solution (UAN)," available at www.cfindustries.com/pdf/UANMSDS.pdf Oct. 25, 2006.
Chabot et al., "Characterization of the vasodilator properties of peroxynitrite on rat pulmonary artery: role of poly (adenosine 5'-diphosphoribose synthase," British Journal of Pharmacology 121:485-490 (1997).
Chang et al., "Arginase modulates nitrix oxide production in activated macrophages," Am. J. Physiol., 274: H342-348, 1998.
Chemical Abstracts Service, "Chemical Abstracts", The American Chemical Society, Liquid Crystals, vol. 104, Jun. 2, 1986.
ColorMaker, 2006.
CPG Sec 565.100 FDA Jurisdiction Over Meat and Poultry Products, 2005.

(56) References Cited

OTHER PUBLICATIONS

Craig, "Betaine in human nutrition," Am J Clin Nutr, 80:539-549,2004.
Creatine from Wikipedia, 2017.
Creatine nitrate from PubChem, 2017.
Cromwell et al., "The Biosynthesis and Metabolism of Betaines in Plants," 1953 Biochem J., 55: 189-192.
Crooks et al., U.S. Patent Application Publication No. 2002/0065323 A1, published May 30, 2002.
Curtis, J., Dec. 6, 2017, "Nitrate-Free Bacon: Myth or Reality", https://firsthandfoods.com/author/jennifer/, pp. 1-2 (Year: 2017).
D. D. Rees, et al., Role of endothelium-derived nitric oxide in the regulation of blood pressure, Proc. Natl. Acad. Sci. USA, vol. 86, pp. 3375-3378 (May 1989).
Danov et al., "Mixed Solutions of Anionic and Zwitterionic Surfactant (Betaine): Surface Tension Isotherms, Adsoprtion, and Relaxation Kinetics," 2004 Langmuir 20: 5445-5453.
Declaration of James L. Bono Under 37 C.F.R. § 1.132 dated Aug. 27, 2014.
Declaration of Richard Chamberlin Dessaignes, Comptes Rendus 1854 Under 37 C.F.R. § 1.132 dated Aug. 15, 2014 filed in Reexam. Control Nos. 90/011,869 and 90/011,869.
Declaration of Richard Chamberlin Under 37 C.F.R. § 1.132 dated Aug. 28, 2014.
Del Compo et al., "Creatinine, creatine and protein in cooked meat products", Food Chemistry, vol. 63, No. 2, pp. 187Y190, 1998.
Del Pilar Garcia-Santos et al., "Reactivity of Amino Acids in Nitrosation Reactions and Its Relation to the Alkylating Potential of Their Products," J. Am. Chem. Soc., 2002, 124(10): 2177-2182.
Dessaignes et al., The Chemist or Chemical & Physical Science, 1854, pp. 594-597.
Dhar et al., Complex Compounds of Acid, Base and Salt with Nitrogenous and Other Organic Substances, in National Academy of Sciences, India, Symposium on Nitrogen, Part 1, Section A, vol. 31, 1961, pp. 76-79.
Dhas, S.A. Martin Britto et al., Growth and Characterization of a New Organic NLO Material; Glycine Nitrate, ScienceDirect, Optics communications 278 (2007) 434-438.
Di Pasquale MG. Amino Acid and Proteins for the Athelete: The Anabolic Edge. CRC Press LLC, 1997, pp. 99-145.
Duncan et al., "Chemical generation of nitric oxide in the mouth from the enterosaliary circulation of dietary nitrate," Nature Medicine, 1 (6): 546-551, Jun. 1995.
Dymatize Nutrition, "Pre-Workout", http://www.dymatize.com/nitric-oxide, Mar. 31, 2014—Advertisement.
Dymatize Nutrition, "Xpand 2x 10 Serving—Dymatize Nutritional Supplements, Whey Protein, Bodybuilding", http://www.dymatize.com/store/p/289-Xpand-2x-10-Servings.html—Advertisement. 2014.
Dymatize® Xpand 2x®, Fruit Punch, Dymatize—GNC, www.gnc.com/product/index.jsp?productId=13180805, Jun. 17, 2013, p. 1-2.
EAS advertisement for "Phosphagen Elite" Joe Welder's Muscle & Fitness, Sep. 2005.
Eaton et al., "Urinary Beta-Alanine Excretion is a Marker of Abnormal as well as Normal Gut Fermentation", Journal of Nutritional & Environmental Medicine (Jun. 2004) 14(2), 121-127.
Edwards et al., "Amino Acids in Foods, Cystine, Tyrosine, and Essential Amino Acid Contents of Selected Foods", Agricultural and Food Chemistry, vol. 3, No. 11 , Nov. 1955.
Elkayam et al. "Prevention of nitrate tolerance with concomitant administration of hydralazine" Can J CArdiol, 1996, vol. 12, suppl C, pp. 17C-21C. (Year: 1996).
Elmore et al., "Compilation of free amino acid data for various food raw materials, showing the relative contributions of asparagine, glutamine, aspartic acid and glutamic acid to the fee amino acid composition", Oct. 2002, JIFSAN Acrylamide in Food Workshop, Chicago. (Year 2002).
English translation of KR-20110015141-A, Feb. 15, 2011, pp. 1-23 (Year: 2011).
Eppendorfer et al., "Free and Total Amino Acid Composition for Edible Pears, Beans, Kale, Spinach, Cauliflower, and Potatoes as Influenced by Nitrogen Fertilisation and Phosphorus Deficiency," J.Sci. Food Agric. 71 449-458, 1996.
Eto et al. publication, Archives of Physiology and Biochemistry, 1995, 103(2):160-4.
Examine.com, "L-Carnitine", Sep. 12, 2014, https://examine.com/supplements/l-carnitine/. (Year:2014).
F. Murad, Cyclic Guanosine Monophosphate as a Mediator of Vasodilation, J. Clin. Invest., vol. 78, pp. 1-5 (Jul. 1986).
F. Ray, Meat Curing, ANSI-3994, OSU.
Fanous, S. "Is Sodium Nitrate Bad for You?", May 20, 2015, Healthline, https://www.healthline.com/health/food-nutrition/is-sodium-nitrate-bad-for-you#1, pp. 1-8. (Year: 2015).
Fayers et al."Nitrate tolerance and the links with endothelial dysfunction and oxidative stress," Br J Clin Pharmacol 56:620-628 (2003).
FDA Regulation 42 FR, 1977.
FDA Regulation 48 FR 1701, Indirect Food Additives; Paper and Paperboard Components, FDA, 1983.
Feelisch et al., Eur J. Pharmacol., 1987, 139(1):19-30.
Fetih et al."Excellent Absorption Enhancing Characteristics of NO Donors for Improving the Intestinal Absorption of Poorly Absorbable Compound Compared with Conventional Absorption Enhancers," Drug Metab. Pharmacokinet. vol. 21(3):222-229 (2006).
Fetih et al."Nitric oxide donors can enhance the intestinal transport and absorption of insulin and [Asu1,7]-eel calcitonin in rats," Journal of Controlled Release 106:287-297 (2005).
Flaherty, 1989, Drugs, 137:523-550.
Fraser et al. publication, circulation, 1983, 67(2): 405-412.
G. M. McKnight, et al., Chemical synthesis of nitric oxide in the stomachfi-om dietary nitrate in humans, Gut, vol. 40, pp. 211-214 (1997).
G. M. McKnight, et al., Dietary nitrate in man: friend or foe?, British Journal of Nutrition, vol. 81, pp. 349-358 (1999).
G. R. J. Thatcher, Serial Review: Mechanisms and Novel Directions in the Biological Applications of Nitric Oxide Donors, Free Radical Biology & Medicine, vol. 37, No. 8, pp. 1122-1143 (2004).
G. Richardson, et al., The ingestion of inorganic nitrate increases gast,-;c S-nitrosothio/ levels and inhibits platelet unction in humans, Nitric Oxide, vol. 7, pp. 24-29 (2002).
G.S. Stokes, et al., Long-Term Effectiveness of Extended-Release Nitrate for the treatment of Systolic Hypertension, Hypertension vol. 45, pp. 380-384 (2005).
Gao et al., "Agmatine: A Novel Endogenous Vasodilator Substance," Life Sciences, 57(8): 83-86, 1995.
Gao et al., Life Science, 1995, 57: 83-86.
Giant Sport Metabolic Bioshock—Workout Supplement, on line, sale product, 2014.
Gibson et al. "Protective role of the epithelium of the small intestine and colon", inflamm. Bowel Dis., 1996, vol. 2, No. 4, pp. 279-302, abstract provided. (Year: 1996).
GNC Mega Men, "GNC Mega Men 90 Caplets", http://www.gnc.com/GNC-Mega-Men-reg/product.jsp? productId=4033432, Apr. 22, 2014.
Godzisz, "Classification and nature of hydrogen bonds to betaine. X-ray, 13C CP MAS and IR description of low barrier hydrogen bonds," Journal of Molecular Structure, 606:123-137,2002.
Grasemann et al., "Oral L-arginine supplementation in cystic fibrosis patients: a placebo-controlled study," Eur Respir J 25:62-68 (2005).
Green et al. publication, Sports Med., 1996, 21(2): 119-146.
Gwartney, D. L, "On the Horizon: Agmatine," Oct./Nov. 1998, PUMP 101:96-97.
Harm J. Knot. "Nitrate Tolerance in Hypertension New Insight Into a Century-Old Problem," Circulation Research vol. 93:799-801 (2003).
Harris et al. "The absorption of orally supplied beta-alanine and its effect on muscle carnosine synthesis in human vastus lateralis" Amino Acids, 2006, vol. 30, pp. 270-289. (Year: 2006).
Harrison, D.G. et al., "The Nitrovasodilators, new Ideas About Old Drugs," Circulation, vol. 87, No. 5, May 1993, pp. 1461-1467).
Hatanaka et al."Stereoselective Pharmacokinetics and Pharmacodynamics of Organic Nitrates in Rats," J Pharmacol Exp Ther. vol. 298(1):346-53 (2001).

(56) References Cited

OTHER PUBLICATIONS

Haussuhl, "Elastic and thermoelastic properties of twelve adducts of betaine," Z Kristallogr, 188:311-320,1989.
Hayashi et al.PNAS 102(38):13681-13686 (2005).
Henriksson et al., Acta Physiol, Sep. 1, 2007, 191:1.
Herbwisdom.com, 2006.
Hoffman et al., "Effect of Creatine and β-Alanine Supplementation on Performance and Endocrine Responses in Strength/Power Athletes", International Journal of Sport Nutrition and Exercise Metabolism, 2006, 16, 430-446, © 2006 Human Kinetics, Inc.—20.
Honikel's publication, Meat Science, 2008,78: 68-76.
Hord et al., "Food sources of nitrates and nitrites: the physiologic context for potential health benefits1-3", Perspective, Am J Clin Nutr 2009;90:1-10, American Society for Nutrition.
http://www.beyondsupplements.com.au/index.php?route=product/, no date given.
http://www.bodybuilding.com/store/fuel-one/6th-gear.html, no date given.
http://www.curezone.org, no date given.
http://www.dymatize.com/store/workoutsupport/M-P-ACT-Energy, no date given.
http://www.ergo-log.com/plaatjes/xpand2x.gif, no date given.
https://nuts.com/cookingbaking/powders/beet.html, 2016.
https://www.thesynergycompany.com/organic-carrot-juice-powder, no date given.
Hui or Shi et al., Handbook of Food Science, Technology, and Engineering, 2006, vol. 4, Chapter 170, p. 170-1-170-9.
Hunter et al., "The Inhibition of Arginase by Amino Acids", Department of Pathological Chemistry, University of Toronto, Canada, Jul. 24, 1944.
Huxtable et al. Physiological Reviews, 72(1):101-142, 1992.
IForce Nutrition product "Potassium Nitrate", 2006.
Ignarro ("After 130 years, the molecular mechanism of action of nitroglycerin is revealed,"[online], Jun. 11, 2002 [retrieved on May 8, 2016] Retrieved from the Internet: <http://www.pnas.org/cgi/content/full/99/12/7816?ck=nck>).
Ignarro et al. publication, The Journal of Pharmacology and Experimental Therapeutics, 1988, 244(1): 181-189.
Ignarro et al., "Pharmacology of Endothelium-derived Nitric Oxide and Nitrovasodilators", The Western Journal of Medicine, Jan. 1991, 154.
Ilczyszyn et al. CAS: 145:83630 2006.
Ingested Nitrate and Nitrite, and Cyanobacterial Peptide Toxins, World Health Organization International Agency for Research on Cancer (2010).
Ionic Liquids ( URL: https://www.organic-chemistry.org/topics/ionic-liquids.shtm ), printed Apr. 2019 (Year: 2019).
Ishii et al., "High glucose augments arginase activity and nitric oxide production in the renal cortex," Metabolism 53(7):868-874 (2004).
J. Abrams, MD, Beneficial Actions of Nitrates in Cardiovascular Disease, The American Journal of Cardiology, vol. 77, pp. 31C-37C (May 30, 1996).
Jablecka et al.Med Sci Monit 10(I):CR29-32 (2004).
Jamalian et al., "Nutritional Value of Middle Eastern Foodstuffs", Jamalian & Pellett : Nutritional Value of Middle Eastern Foodstuff's. IV, Dec. 1967.
Joy et al., "A multi-ingredient, preworkout supplement is apparently safe in healthy males and females," Food & Research, 59:27470, 2015.
K. Cosby, et al., Nitrite reduction to nitric oxide by deoxyhemoglobin vasodilates the human circulation, Nature Medicine, vol. 9, No. 12, pp. 1498-1505(Dec. 2003).
K. Tsuchiya, et al., Malfunction of Vascular Control in Lifestyle-Related Diseases: Formation of Systemic Hemoglobin-Nitric Oxide Complex (HbNO) From Dietary Nitrite, J. Pharmacol Sci, vol. 96, pp. 395-400 (2004).
Kemmerer et al. publication, J. Nutr., 1949, 38(4): 527-33.
Kendrick et al., "The effect of 4 weeks B-alanine supplementation and isokinetic training on carnosine concentrations in type I and II human skeletal muscle fibres", Eur J Appl Physiol (2009) 106:131-138, Feb. 12, 2009.
Kenechuwu et al. J. Microencapsul, 2017, 34(6):592-609.
Kernohan et al., "An oral yohimbine/L-arginine combination (NMI 861) for the treatment of male erectile dysfunction: a pharmacokinetic, pharmacodynamic and interaction study with intravenous nitroglycerine in healthy male subjects", British Journal of Clinical Pharmacology, © 2004 Blackwell Publishing Ltd.
Kou et al. applicaiton No. 200410009958.3, 2005.
Kramer et al., U.S. Patent Application Publication No. 2009/076110 A1 published Mar. 19, 2009.
L. Appel, et al., A Clinical Tr;al of the Effects of Dietal J1 Patterns on Blood Pressure, N. Engl. J. Med., 336:16, pp. 1117-1124 (Apr. 17, 1997).
L. Brunton, An Address on Blood Pressure In Man: Its estimation and indications for treatment, The British Medical Journal, pp. 64-67 (Jul. 10, 1909).
L. Brunton, et al., An Address on Longevity and the Means of Attaining It, The Lancet, vol. 168, Issue 4342, pp. 1330-1335 (Nov. 17, 1906).
L. Noah et al., Starting from Scratch?: Reinventing the Food Additive Approval process, Boston Univ. L. Rev. vol. 78:329, pp. 329-443 1998.
L. Stryer, Biochemistry, Third Edition, W. H. Freeman and Company, pp. 15-24, 261-268, 499-502, and 933-936, New York, 1988.
Large Wendy, "Circuit training combines aerobic and anaerobic workouts into one," News Journal (Mansfield Ohio), Sep. 5, 2004.
Larsen et al. publication, New England Journal of Medicine, 2006, 2792-2793.
Larsen, Effects of dietary nitrates on oxygen cost during Exercise, B. Acta Physiol 191(1 ):59-66 (2007).
Lewis et al. publication, Pharmacol. Biochem Behav, 2007, 88(1): 114-21.
Ilczyszyn et al. 13C chemical shift tensors of hydrogen bonded amino acids: Relations between experimental and calculated results. Chemical Physics 323 (2006) 231-242.
Luigi et al., Med. Sc.i Sports Exerc., 1999, 31(12): 1748-54.
Lundberg et al., "Cardioprotective effects of vegetables: Is nitrate the answer?", Science Direct, Jan. 2006.
Lundberg et al., "The nitrate-nitrite-nitric oxide pathway in physiology and therapeutics", 2008 Nature Publishing Group, Feb. 2008, vol. 7.
Lundberg et al., Arterioscler. Thromb. Vasc. Biol., 25:915-922 (2005).
Lundberg et al., Inorganic nitrate is a possible source of systemic generation of nitric oxide, Free Radical Biology Medicine, vol. 37, No. 3. pp. 395-400, 2004.
Luscher, "Endogenous and exogenous nitrates and their role in myocardial ischaemia," Br. J. Clin. Pharmacol. 34:29S-35S (1992).
Magg, G.W., Hecker, R.J. and Whitaker, P.A., "Nitrogenous Compounds in Sugarbeet Juices", Journal of the American Society of Sugar Beet Technologists, 1972; vol. 17, No. 2pp. 154-164.
Marconi, Int. J. Sports Med, 11 (1990):1-14.
Material Safety Data Sheet—L-leucine MSDS.
Material Safety Data Sheet—Taurine.
Material Safety Data Sheet—Agmatine sulfate salt.
Material Safety Data Sheet-B—Alanine MSDS.
Material Safety Data Sheet-L—Arginine.
Material Safety Data Sheet-L—Glutamine MSDS.
Material Safety Data Sheet-L—Norvaline.
Maynard et al., "High Levels of Dietary Carnosine are Associated with Increased Concentrations of Carnosine and Histidine in Rat Soleus Muscle," J. Nut. 131:287-290 (2001).
Merriam-Webster definition of supplement https://www.merriam-webster.com/dictionary/supplementlaccessed Jun. 20, 2019] (Year: 2019).
Miller, Elements of Chemistry—Theoretical and Practical, Longsmans, Green, Reader and Dyer, 1969, pp. 757-770.
Ming et al.Circulation 110:3708-3714 (2004).
Mostad et al."Crystal and molecular structure of DL-methionine nitrate," CAS 104:1975, 43 (1986).

(56) References Cited

OTHER PUBLICATIONS

Mostad, A., Zeitschrift fur Kristallographie, 172: 175-182, 1985.
MrSupplement.com product dietary supplement Creatine Nitrate, 2006.
Muramoto, J., "Comparison of Nitrate Content in Leafy Vegetables from Organic and Conventional Farms in California" Center for Agroecology and Sustainable Food Systems University of California, Santa Cruz, 1999.
Nature's Best advertisement for "Perfect L-Glutamine" Joe Weider's Muscle & Fitness, Sep. 2005.
Niu et al."Vasorelaxant effect of taurine is diminished by tetraethylammonium in rat isolated arteries," European Journal of Pharmacology 580:169-174 (2008).
NutrabioBCAA2500, 2006.
Oka et al.Vasc Med 10:265-274 (2005).
Optimum Nutrition advertisement for "Adenergy Stack" Joe Weider's Muscle & Fitness, Sep. 2005.
Pariser et al. Cutis, 1994, 54(1): 43-44.
Parker et al., The Effect of Supplemental L-Arginine on Tolerance Development During Continuous Transdermal Nitroglycerin Therapy, J. of Am. Coll. of Cardiology, 39(7): 1199-1203, 2002.
PEScience High Volume, 2007.
Petersson et al., "Dietary nitrate increases gastric mucosal blood flow and mucosal defense," Am. J. Physiol. Gastrointest. Liver, 292: G718-G724, 2007.
Petrosyan et al., J. Molecular Structure, 794: 160-167, 2006.
Piccolo et al. CAS: 138: 1375892003.
Pickering et al., Why Don't We Use Nitrates to Treat Older Hypertensive Patients?, Journal of Clinical Hypertension, vol. 7, No. 11, pp. 685-690 (Nov. 2005).
Pischel et al. CAS: 134:71896, 2001.
Pradhan et al., Journal of Chemical and Engineering Data, 2000, 45(1):140-143.
ProArgi 9 Supplement Website: ProArgi-9 Plus FAQ, "ProArgi 9 Plus Site", http://proargi9site.blogspot.com/p/proargi-9-plus-faq.html, Apr. 22, 2014.
Professor of Udinsev. Nitrates and physical performance. Siberian fiber. Sep. 8, 2018. [on-line] [ retrieved on Jun. 29, 2020] (Retrieved from the Internet: https://tfzp.ru/zdorovyj-obraz-zhizni/v/nitraty/nitraty-i-fizicheskaya-rabotosposobnostO, p. 2, paragraph 2-p. 3, paragraph 1, p. 4, paragraph 1.
PS Nutrition Creatine Nitrate, on line, sale producr, 2014.
QuadraLean by RSP Nutrition, Bodybuilding.com, 2006.
R.C. Harris et al., "The Influence of Beta-Alanine Supplementation and Training on the Muscle Carnosine Content in Human v. lateralis, and the Effect of This on Exercise Performance," Amino Acids 29:12-13 (2005).
Rajkumar and Ramakrishnan, "Infrared and Roman Spectra of L-Valine Nitrate and L-Leucine Nitrate", Journal of Raman Spectroscopy, 2000. p. 1107-1112, vol. 31. John Wiley & SonsLtd.
Rajkumar et al., "Infrared and Raman spectra of DL-aspartic acid nitrate monohydrate," Spectrochimica Acta Part A, 54:1527-1532, 1998.
Ramaswamy et al."Vibrational spectroscopic studies of L-argininium dinitrate," J. Raman Spectrosc. 34:50-56 (2003).
Rao et al."Structure and Conformational Aspects of the Nitrates of Amino Acids and Peptides. I. Crystal Structure of Glycylglycine Nitrate," Acta Cryst. B29:2379-2388 (1973).
Riens et al., "Amino Acid and Sucrose Content Determined in the Cytosolic, Chloroplastic, and Vacuolar Compartments and in the Phloem Sap of Spinach Leaves1", Plant Physiol. (1991) 97, 227-233, Apr. 6, 1991.
Rimando et al., "Determination of Citrulline in Watermelon Rind", Journal of Chromatography A, 1078 (2005) 196-200, May 2, 2005.
Rombauer, Irma S., "Joy of Cooking", 75th Anniversary, Scribner, New York, 2006, p. 163 (2006).
Romero et al., "Therapeutic Use of Citrulline in Cardiovascular Disease," Cardiovascular Drug Reviews 24(3-4):275-290 (2006).
Rosen et al. "Nutrient Management for Commercial Fruit & Vegetable Crops in Minnesota" University of Minnesota extension Service, 2005 pp. 35-36 <https://conservancy.umn.edu/bitstream/handle/11299/51272/5886.pdf?sequence=1>.
RSPReGenBCAA, 2006.
Ruel et al., "Modulation in Angiogenic Therapy randomized controlled trial," J Thorac Cardiovasc Surg 135:762-770 (2008).
Rytlewski et al., Effects of prolonged oral supplementation with L-arginine on blood pressure and nitric oxide synthesis in preeclampsia, Eur J Clin Lnvest 35(1):32-37 (2005).
Rytlewski et al.European Journal of Obstetrics & Gynecology and Reproductive Biology 138:23-28 (2008).
S. Moncada, et al., The L-Arginine:Nit ic Oxide Pathway, Journal of Cardiovascular Pharmacology, 17(Suppl. 3):S 1-S9 1991).
S. Ramaswamy, Acta Cryst., E58, 646-648 (2002).
Sader et al., "Endothelial Function, Vascular Reactivity and Gender Differences in the Cardiovascular System", Cardiovascular Research 53 (2002) 597-604, Aug. 21, 2001.
Sale et al. Effect of beta-alanine supplementation on muscle carnosine concentrations and exercise performance. Amino Acids, 39:321-333, 2010.
San Corporation dietary supplement containing creatine nitrate, 2006.
Santamaria et al. "A survey of nitrate and oxalate content in fresh vegetables" Journal of the Science of Food and Agriculture, 1999, vol. 79, 1882-1888. (Year: 1999).
Sastre et al."Metabolism of agmatine in macrophages: modulation by lipopolysaccharide and inhibitory cytokines," Biochem. J. 330:1405-1409 (1998).
Schaefer et al., Intl. J. of Sports Medicine, 2002, 23(6):403-407.
Schulbach et al., "Guide to nitrogen quick-tests for vegetables wit the 'cardy' nitrate meter" FREP Contract # 95/0582.
Schulz et al., "Functional and Biochemical Analysis of Endothelial (Dys)function and NO/cGMP Signaling in Human Blood Vessels with and without Nitroglycerin Pretreatment," Circulation 105:1170-1175 (2002).
Schwedhelm et al., "Pharmacokinetic and pharmacodynamics properties of oral L-citrulline and L-arginine: impact on nitric oxide metabolism," Br J Clin Pharmacol 65(1):51-59 (2007).
Sen et al. Journal of Association of Official Analytical Chemists, 61(6): 1389-1394, 1978.
Shen et al. publication, Acta Physiol. Scand, 2000, 168(4): 675-86.
Shen, W., Nitric oxide production and NO synthase gene expression contribute to vascular regulation during exercise, Med. Sri Spnrts Fxerc., vol. 27,No. 8, pp. 1125 1134(Aug. 1995).
Shiraki et al., "The hypotensive mechanisms of the new anti-anginal drugN-(2-Hydroxyethyl) Nicotinamide Nitrate (SG-75) in beagle dogs," Japan. J. Pharmacol. vol. 31:921-929 (1981).
Simplico et al. "Prodrus for Amines", Molecules 2008, vol. 13, pp. 519-547.
Slart et al., "Nitrate Administration Increases Blood Flow in Dysfunctional but Viable Myocardium, Leading to Improved Assessment of Myocardial Viability: A PET Study," J Nucl Med 47:1307-1311 (2006).
Smith et al."Nitric oxide precursors and congenital heart surgery: A randomized controlled trial of oral citrulline," J Thorac Cardioasc Surg 132:58-65 (2006).
Sridhar et al, "L-Aspartic Acid Nitrate-L-Aspartic Acid," Acta Cryst. E58:o1372-o1374 (2002).
Srinivasan et al., "L-phenylalanine-nitric acid (2/1)," Acta Crystallographica E57:0916-0918, 2000.
Stephany et al. "The Intake of Nitrate, Nitrite and Volitile N-Nitrosamins and the Occurrence of Volatile N-nitrosamines in human urine and Veal Calves" IARC Scientific Publications, Jan. 1978, vol. 19, pp. 443-460. (Year: 1978).
Stephenson, T., "How children's responses to drugs differe from adults," Br. J. Clin. Pharmacol., 59(6):670-673, 2005.
Stetson, C., "Characteristics of Adults vs. Children." [retrieved on May 4, 2016], Retrieved from the Internet <URL: http://www.ehow.com/info 8501147 characteristics-adults-vs-children.html>.
Stout et al., "Effects of B-Alanine Supplementation on the onset of Neuromuscular Fatigue and Ventilatory Threshold in Women", Amino Acids (2006), Springer-Verlag 2006.

(56) References Cited

OTHER PUBLICATIONS

Stryer, Lubert, Biochemistry, Third Edition, W.H. Freeman and Company, New York: 1988, pp. 16-23, 233-236, 500-502 and 934-936.
Sugino et al., "L-ornithine supplementation attenuates physical fatigue in healthy volunteers by modulating lipid and amino acid metabolism," Nutrition Research, 2008, 28:738-743.
Summary of Studies of B-Alanine and sports performance, "Studies of B-Alanine Supplementation on Exercise Capacity or Performance", Nov. 2011.
Swensen et al. publication, Intl. J. of Sports medicine, 1994,15(7):430-4.
Takahashi et al."Characterization of the influence of nitric oxide donors on intestinal absorption of macromolecules," International Journal of Pharmaceutics 286:89-97 (2004).
Tan et al., "Taurine protects against low-density lipoprotein-induced endothelial dysfunction by the DDAH/ADMA pathway," Vascular Pharmacology 46:338-345 (2007).
Tannebaum et al., "Inhibition of nitrosamine formation by ascorbic acid," Am. J. Clin. Nutr. 53: 2475-2505, 1991.
Tao, Guo-Hong et al., new Generation Ionic Liquids: Cations Derived From Amino Acids, The Royal Society of Chemistry, ChemComm, Jun. 9, 2005, 3562-3564.
Taurine from Nutrabio, 2006.
Teragawa et al. (Heart, 86:212-216, 2001) Magnesium causes nitric oxide independent coronary artery vasodilation in humans.
Terzyan et al., "L-Arginine Nitrates," Journal of Molecular Structure 687:111-117 (2004).
Thandani, U. "Challenges with Nitrate Therpy and Nitrate Tolerance: Prevalence , Prevention, and Clinical Relevance" Am J Cardiovasc Drugs, 2014, vol. 14, pp. 287-301. (Year: 2014).
The product APS Creatine Nitrate , for sale, 2014.
The product Isoleucine nitrate power with a Brand name Hobid, for sale, 2014.
The product L-glutamine nitrate power with a Brand name Hobid, for sale, 2014.
The product L-Leucine nitrate power by Body Ripped, for sale, 2014.
The product valine nitrate power with a Brand name Hobid, for sale, 2014.
U.S. Food & Drug Administration document with respect to 21 CFR §184.1878 for thiamine mononitrate (Year: 2018).
Urakami, M. et al., "Relationship between Structure and Permeability of Tryptophan Derivatives Across Human Intestinal Epithelial (Caco-2) Cells.", Z. Naturforsch., (2003), vol. 58C, pp. 135-142, XP055127040.
USDA and HHS Agencies Work Together to Examine the Jurisdiction of Certain Food Categories, USDA & FDA, 2005.
USDA Regulation 64 FR 72168, Food Ingredients and Sources of radiation Listed or Approved for Use in the Production of Meat and Poultry, 1999.
Vandenberghe et al. publication, J. Appl physiol, 1997, 83:2055-2063.
VS Kouzenkov, AL Krushinsky , "Sodium potassium effect on development of nerological deficiency in experimental model of brain ishemia", Moscow University Bulletin Ser. 16. Biology, (20140000), vol. 4, pp. 9-14, XP055831436.
Vytech advertisement for "Nitrobol Extreme" Joe Welder's Muscle & Fitness, Sep. 2005.
Walker et al., Food additive and Contaminants, 1990, 7(6):717-768.
Watt et al., "The Chemist, A Monthly Journal of Chemical & Physical Science", vol. 1, London; Samuel Highley, 32 Fleet Street, 1854.
Watts, "A Dictionary of Chemistry and the Allied Branches of Other Sciences", Library of the University of California, Aug. 1808.
Weitzberg et al., "Dietary Nitrate—A Slow Train Coming", J Physiol 589.22 (2011) pp. 5333-5533, 2011 The Authors. Journal compilation, 2011 The Physiological Society.
Wheatley et al., "Arginine deprivation and tumor cell death arginase and its inhibition," Molecular and Cellular Biochemistry, 244: 177-185, 2003.
White, Handler and Smith, Principles of Biochemistry, Fifth Edition, McGrawy-Hill, New York:1973, pp. 89-95.
Wilson et al., "Beta-Alanine-Bad Ass Supplement", Iron Man Magazine, Oct. 13, 2010.
Winter et al., "N-Nitrosamine Generation From Ingested Nitrate Via Nitric Oxide in Subjects With and Without Gastroesophageal Reflux," Gastroenterology, 2007, 133:164-174.
Ximenes, M. I. N., et al., "Polarographic determination of nitrate in vegetables" Talanta 51 (2000) 49-56.
Xu et al., "Composite medical preparation for promoting hair growth," CAS: 143:103285 (2005).
Zhang et al. publication, Amino acids, 2004, 26:203-207.
Zhu et al., "Expression of Human Arginine Decarboxylase, the Biosynthetic Enzyme for Agmatine", NIH Public Access, Biochim Biophys Acta. Jan. 22, 2004; 1670(2): 156-164.
Ziegenfuss et al., "Effect of a Supplement Containing Primarily Beta Alanine, Arginine, Creatine Malate, and Glycerol Monostearate on Exercise-Induced Changes in Lean Mass of the Arms", Journal of the International Society of Sports Nutrition 2008, 5(Suppl 1):p. 16 doi:10.1186/1550-2783-5-S1-P16.
A. Patrician et al., "Dietary nitrate enhances arterial oxygen saturation after dynamic apnea", Scand J Med Sci Sports, (20170000), vol. 27, doi:10.1111/sms.12684, pp. 622-626, XP055943939.
Acetyl/propionyl Carnitine from BodyBuilding, 2006. 1 page.
Arnold et al. (Biochemistry 99;38(15):4750-4756) (Year: 1999) 7 pages.
Curry, M.D., Steven, "Methemoglobinemia", Ann Emerg Med, 11, 214-221, 1982.
Dymatize® Xpand 2x®, Fruit Punch, Dymatize GNC, www.gnc.com/product/index.jsp?productId=13180805, Jun. 13, 2013. 4 pages.
Ekblom et al., The New England Journal of medicine, 2006, 335; 26, pp. 2792-2793.
Gago et al., Red wine-dependent reduction of nitrite to nitric oxide in the stomach, Free Radical Biology and Medicine 43:1233-1242, 2007. 10 pages.
George Barger, M.A., D.Sc., "The Simpler Natural Bases", Monographs on Biochemistry, U.C.D. Library, Nov. 23, 1960, Digitized 2007. 232 pages.
Gwartney, "On the Horizon: A Glimpse into the Future of Supplementation," in Pump magazine, Nov./Dec. 1998 4 pages.
H. Yamasaki, "Blood nitrate and nitrite modulating nitric oxide bioavailability: potential therapeutic functions in COVID-19", Nitric Oxide, vol. 103, doi:https://doi.org/10.1016/j.niox. 2020.07.00 5, (Jul. 23, 2020), pp. 29-30, XP055943941.
Mirvish, SS (Annals of New York Academy of Sciences. 1975; pp. 175-180) (Year: 1975).
Qin, Yu, et al., "Portable Nitric Oxide (NO) Generator Based on Electrochemical Reduction of Nitrite for Potential Applications in Inhaled NO Therapy and Cardiopulmonary Bypass Surgery", Mol Pharmaceutics, http://pubs.acs.org, 37 pages, 2017.
Shinbo, Toshihiro, et al., "Breathing nitric oxide plus hydrogen gas reduces ischemia-reperfusion injury and nitrotyrosine production in murine heart", Am J Physiol Heart Circ Physiol, 305, H542-H550, 2013.
Sulcius, A. (J. Chem. Educ. 2015,92:1971-1972). (Year: 2015) 6 pages.
Ashenhurst ([online] retrieved on Aug. 18, 23 from: https://www.masterorganicchemistry.com /2018/02/28/ amides- properties-synthesis-and-nomenclature/ 3 pages) (Year: 2023).
Carbonyl diamine [online] retrieved on Aug. 18, 23 from: https://www.chembk.com/en/chem/Carbonyl%20diamine;1 page.(Year: 2023).

* cited by examiner

METHOD OF TREATING MIGRAINES AND HEADACHES

CROSS REFERENCE TO RELATED APPLICATIONS

This application claims priority to U.S. patent application Ser. No. 17/670,383, filed Feb. 11, 2022, which claims priority to PCT Application No. PCT/US22/16231, filed Feb. 11, 2022, which claims priority to both U.S. Provisional Patent Application No. 63/148,523, filed on Feb. 11, 2021, and U.S. Provisional Patent Application No. 63/180,039, filed on Apr. 26, 2021, the contents of each of which are incorporated herein by reference in their entireties.

This application also claim priority to U.S. patent application Ser. No. 17/525,841, which claims priority to U.S. Provisional Patent Application No. 63/113,114, filed Nov. 12, 2020; U.S. Provisional Patent Application No. 63/148,517, filed Feb. 11, 2021; and U.S. Provisional Patent Application No. 63/232,852, filed Aug. 13, 2021, the contents of each of which are hereby incorporated by reference in their entireties.

BACKGROUND

The 2015 Global Burden of Disease (hereinafter "2015 GBD") Neurological Disorders Collaborator Group noted that a broad group of neurological disorders accounts for 250.7 million Disability-Adjusted Life Years (DALYs), which is about 10.2% of global DALYs. The report also noted that DALYs caused by this broad group of neurological disorders increased by 7.4% in the last 25 years. Based on the Institute for Health Metrics and Evaluation's data, the same group of neurological disorders accounts for 85.6 million Years Lived with a Disability (YLDs) in 2015, which is 10.7% of global YLDs, which unfortunately increased by 55.2% (YLDs were 55.1 million in 1990) in the last 25 years. A considerable portion of disability is caused by headache disorders. The 2015 GBD reported that tension-type headache (TTH) and migraine are the most common conditions and they account for 60.3% of YLD associated to brain conditions (respectively, 7.2 and 44.5 million YLDs in 2015). These statistics are no surprise, as headaches are one of the most common pain conditions in the world, with up to 75% of adults worldwide having had a headache in the past year.

Headaches can be divided into over 150 types of headaches, but they all fall into two main categories: primary and secondary headaches. Primary headaches are those that aren't due to another medical condition, while secondary headaches are related to another medical condition. Migraines, cluster headaches, new daily persistent headaches, and tension headaches are the most well-known primary headache conditions.

Among primary headaches, migraine is a strong headache that often comes with nausea, vomiting, and sensitivity to light. The prevalence and burden of self-reported migraine and severe headache in the US adult population is high, affecting roughly 1 out of every 6 Americans and 1 in 5 women over a 3-month period (15.3% overall [95% CI 14.75-15.85], 9.7% of males [95% CI 9.05-10.35] and 20.7% of females [95% CI 19.84-21.56]). Migraines can last hours or days.

As an example of a secondary headache, post-COVID-19 headache is a persistent headache that develops after having COVID-19. Post-COVID-19 headache can last for weeks or even months after testing negative for the virus. While anyone can develop post-COVID-19 headache, migraine sufferers are more likely to see an increase in the frequency and intensity of their migraine attacks after a COVID-19 infection.

Regardless of the category of headaches, headache pain results from signals interacting among the brain, blood vessels and surrounding nerves, where an unknown mechanism activates specific nerves that affect muscles and blood vessels that send pain signals to the brain. Thus, the causes of headaches remain unclear.

As a result, management and treatment of headaches has primarily been figuring out triggers and minimizing the numbers of headache incidents. This is because there are limited options for pain management, and many medications gradually lose effectiveness. For some medications, increased use can cause further headaches.

Accordingly, additional treatment options for headache pain management are needed.

SUMMARY

The disclosure relates to compositions, kits, and methods related to treating a headache, for example a migraine, through nitric oxide therapy comprising orally administering to a subject suffering from a migraine an effective amount of an elemental metal and an effective amount of a source of nitrate anion. In other aspects, the nitric oxide therapy is an inhalation therapy. In such embodiments, the method comprises combining a source of nitrate anion and an elemental metal in an acidic solution in a vessel capable of housing liquid and gaseous constituents thereby producing NO gas. Thus, disclosed herein are compositions and kits comprising an effective amount of an elemental metal and an effective amount of a source of nitrate anion. In some aspects, the compositions and kits further comprise a source of an acid. In particular implementations, the kits further comprise a vessel capable of housing liquid and gaseous constituents.

The elemental metal is selected from the group consisting of: elemental magnesium, elemental calcium, elemental lithium, elemental zinc, elemental sodium, elemental potassium, elemental beryllium, elemental rubidium, elemental cesium, elemental aluminum, elemental gallium, elemental indium, elemental tin, elemental bismuth, elemental scandium, elemental titanium, elemental vanadium, elemental chromium, elemental manganese, elemental cobalt, elemental manganese, elemental scandium, elemental titanium, nickel, elemental copper, elemental zinc, elemental yttrium, elemental zirconium, elemental niobium, elemental molybdenum, elemental technetium, elemental ruthenium, elemental rhodium, elemental palladium, elemental silver, elemental cadmium, elemental lanthanum, elemental hafnium, elemental tantalum, elemental tungsten, elemental rhenium, elemental osmium, elemental iridium, elemental platinum, elemental gold, elemental manganese and elemental iron.

In particular implementations, the elemental metal is selected from the group consisting of: elemental magnesium, elemental calcium, elemental lithium, elemental zinc, elemental potassium, elemental sodium, elemental beryllium, elemental barium, and elemental iron. In other embodiments, the elemental metal is elemental magnesium and/or elemental zinc.

In some aspects, the source of nitrate anion is a nitrate salt or a botanical source of nitrate. For example, the source of nitrate anion may be potassium nitrate, sodium nitrate, or magnesium nitrate. The botanical source of nitrate may be beetroot extract or *Amaranthus* extract.

The pH of the acidic solution may be between 0.1 and 6.9, for example, between 2 and 4. In certain implementations, the method further comprises dissolving an acid powder in a solvent (for example water) to produce the acidic solution. In some implementations, the acid powder is citric acid, malic acid, or fumaric acid. In a particular embodiment, the acidic solution is produced form dissolving the acid powder in 1 ml to 10000 ml water.

In some aspects, the composition is in the form of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof. The composition may further comprise an acceptable additive and/or an acceptable carrier. The acceptable additive may be selected from at least one member from the group consisting of: a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, and a thickener. The acceptable carrier may be selected from at least one member from the group consisting of: an excipient, a lubricant, a binder, a disintegrator, a diluent, an extender, a solvent, a suspending agent, a dissolution aid, an isotonization agent, a buffering agent, a soothing agent, and an amphipathic lipid delivery system. In some aspects, the composition is in a form suitable for oral administration. In other aspects, the composition is in a form suitable for inhalation of the gases produced when in contact with an acidified solvent.

DETAILED DESCRIPTION

Figure 1:
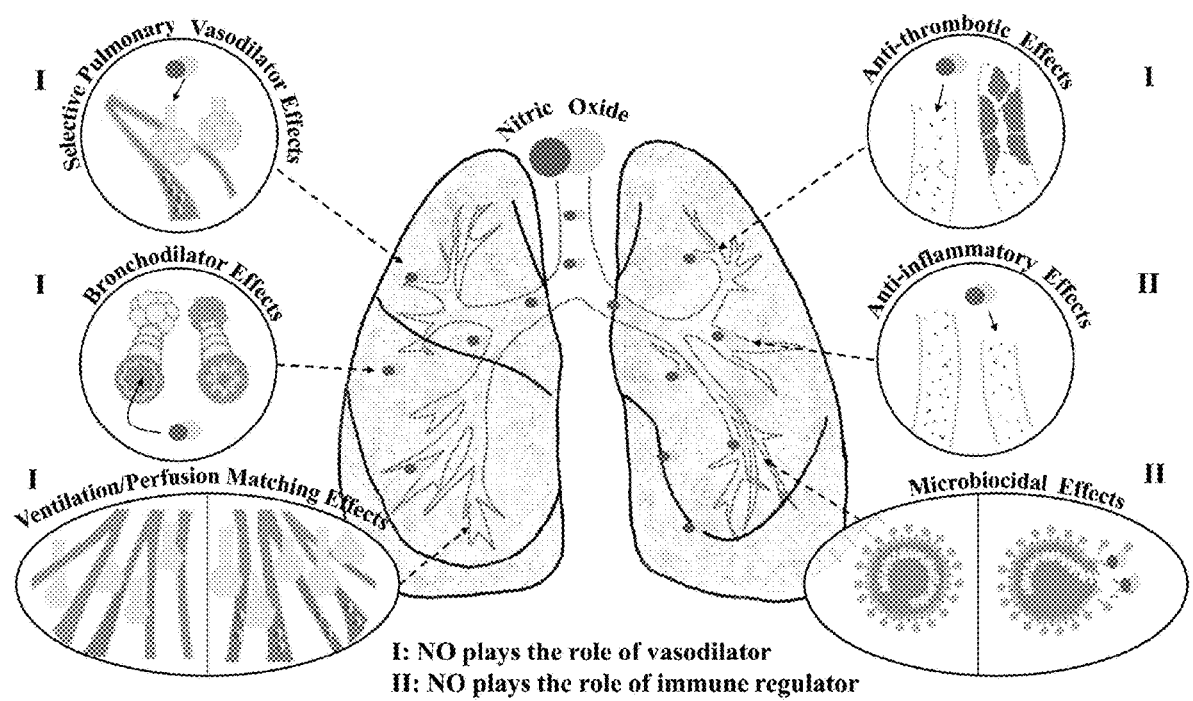
FIG. 1 depicts various pathways in which NO functions in the lungs.
Figure 2:
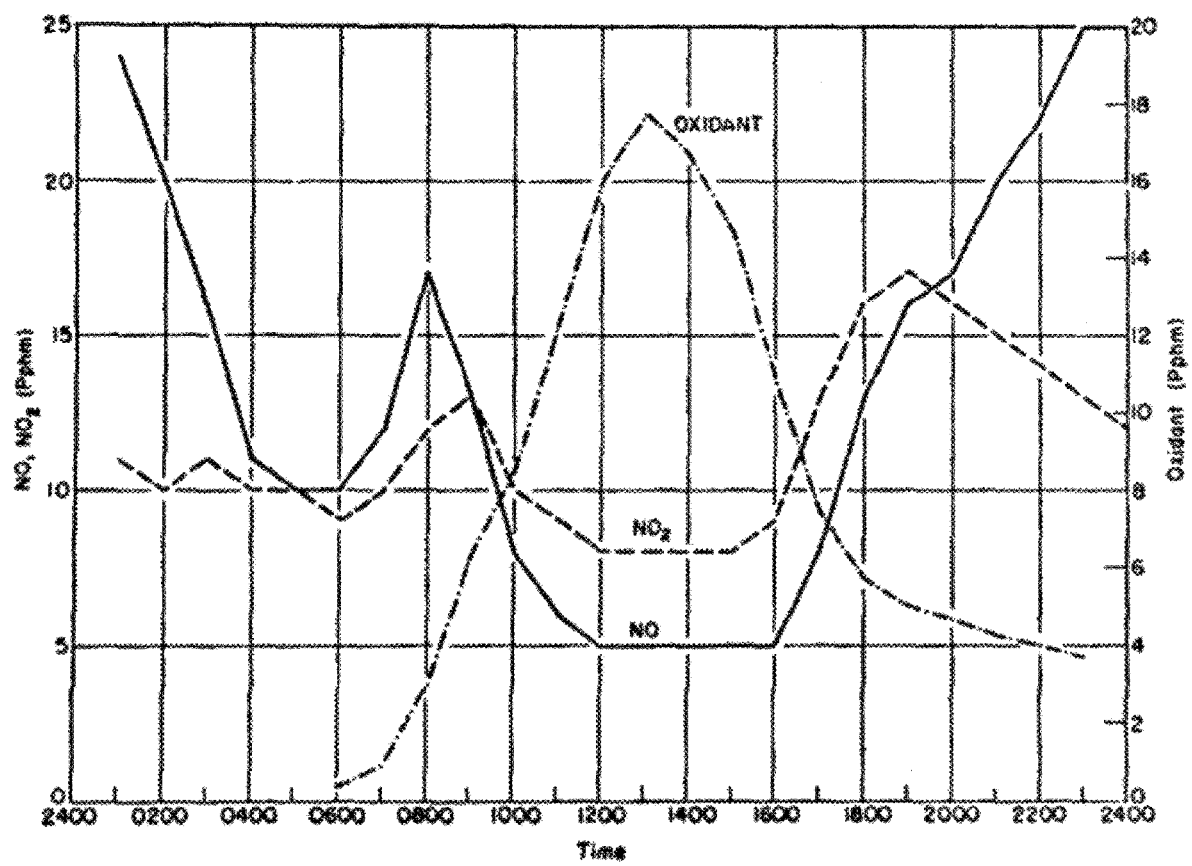
FIG. 2 depicts a quantitative analysis of nitric oxide in the presence of nitrogen dioxide at atmospheric concentrations.

Detailed aspects and applications of the disclosure are described below in the following detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant art, that implementations of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "about" refers to a deviation no more than 5% of the given value, for example a deviation of 3%, 2%, 1%, 0.5%, or 0.1% of the given value.

As used herein, the term "acceptable" is a phrase used in its broadest sense and may describe ingredients of a composition that meet Food and Drug Administration (FDA) standards, United States Pharmacopeia (USP) standards, US Department of Agriculture (USDA) standards for food-grade materials, commonly accepted standards of the nutritional supplement industry, industry standards, botanical standards, or standards established by any individual. These standards may delineate acceptable ranges of aspects of ingredients of a composition such as edibility, toxicity, pharmacological effect, or any other aspect of a chemical, composition, or preparation used in implementations of a composition.

As used herein, the term "composition" refers to both a mixture of ingredients or constituents as well as a combination of capsules that contains different ingredients or constituents. Accordingly, in certain embodiments, a composition encompasses separate capsules that are packaged together and are meant to be taken together.

As used herein, the term "elemental metal" refers to the neutral-charged state of a metal element, in other words, a metal in its elemental form and not in a salt form or charged form (exemplary salt forms and charged forms include the oxide, hydroxide, carbonate, chloride, lactate, citrate, aspartate, glycinate, and gluconate of the metal). As such, as used herein, elemental metals and salts of the same metal are different constituents. A description that a composition comprises an elemental metal cannot be satisfied by the presence of a metal salt, and vice versa. For example, a composition that consists of magnesium citrate is not a composition that comprises elemental magnesium in spite of any description that magnesium citrate provides some amount of elemental magnesium. The elemental metals described herein include elemental magnesium, elemental calcium, elemental lithium, elemental zinc, elemental sodium, elemental potassium, elemental beryllium, elemental rubidium, elemental cesium, elemental aluminum, elemental gallium, elemental indium, elemental tin, elemental bismuth, elemental scandium, elemental titanium, elemental vanadium, elemental chromium, elemental manganese, elemental cobalt, elemental manganese, elemental scandium, elemental titanium, nickel, elemental copper, elemental zinc, elemental yttrium, elemental zirconium, elemental niobium, elemental molybdenum, elemental technetium, elemental ruthenium, elemental rhodium, elemental palladium, elemental silver, elemental cadmium, elemental lanthanum, elemental hafnium, elemental tantalum, elemental tungsten, elemental rhenium, elemental osmium, elemental iridium, elemental platinum, elemental gold, elemental manganese, and elemental iron.

The term "mesh" describes the size of an abrasive particle. When the mesh size (or grade) of a particle is reported, it reports the mean or average diameter of particles in that mesh size or grade. When two numbers are used in reference to the mesh size of a particle, this indicates that all of the particles in that grade of product are within that range of mesh sizes (e.g., mesh size 80-100).

U.S. mesh size (or U.S. sieve size) is defined as the number of openings in one square inch of a screen. For example, a size 36 mesh screen will have 36 openings while a size 150 mesh screen will have 150 openings. The size of screen (one square inch) is constant, so a higher mesh number will mean a smaller screen opening and thus refer to smaller particles. Generally, a U.S. mesh size is measured using screens down to size 325 mesh (325 openings in one square inch). Sometimes the mesh size of a product is noted with either a minus (−) or plus (+) sign. These signs indicate that the particles are either all smaller than (−) or all larger than (+) the mesh size. For example, a product identified as −100 mesh would contain only particles that passed through a 100 mesh screen. A +100 grade would contain particles that did not pass through a 100 mesh screen. When a grade of product is noted with a dash or a slash it indicates that the product has particles contained within the two mesh sizes. For example, a 30/70 or 30-70 grade would only have particles that are smaller than 30 mesh and larger than 70 mesh.

Table 1 depicts a mesh conversion chart, which shows the approximate size in inches and microns for various mesh sizes. These values are generally accepted as accurate but are approximates, because the thickness of the wire used to make a specific screen will vary the number of openings in the one square inch. Most grades below 325 mesh are indicated by the micron size as these sizes are not manufactured using screens.

TABLE 1

Mesh conversion chart.

| US Mesh | Micron | Inches | US Mesh | Micron | Inches |
| --- | --- | --- | --- | --- | --- |
| 4 | 4,750 | 0.187 | 80 | 165 | 0.0065 |
| 5 | 4,000 | 0.157 | 90 | 145 | 0.0057 |
| 6 | 5,350 | 0.132 | 100 | 149 | 0.0059 |
| 7 | 2,800 | 0.111 | 120 | 125 | 0.0049 |
| 8 | 2,360 | 0.0937 | 140 | 105 | 0.0041 |
| 10 | 2,000 | 0.0787 | 150 | 89 | 0.0035 |
| 12 | 1,700 | 0.0661 | 170 | 88 | 0.0031 |
| 14 | 1,400 | 0.0555 | 180 | 76 | 0.003 |
| 16 | 1,200 | 0.0473 | 200 | 75 | 0.0029 |
| 18 | 1,000 | 0.0394 | 220 | 63 | 0.0025 |
| 20 | 850 | 0.0331 | 240 | 53 | 0.002 |
| 24 | 690 | 0.027 | 280 | 44 | 0.0015 |
| 30 | 560 | 0.022 | 320 | 36 | 0.0012 |
| 36 | 485 | 0.019 | 400 | 23 | 0.00087 |
| 40 | 425 | 0.016 | 500 | 19 | 0.00075 |
| 46 | 355 | 0.014 | 600 | 16 | 0.00065 |
| 54 | 305 | 0.012 | 800 | 12 | 0.00047 |
| 60 | 250 | 0.01 | 1,000 | 9 | 0.00028 |
| 70 | 210 | 0.0083 | 1,200 | 6 | 0.00024 |

The present disclosure relates to the surprising discovery that administering a source of nitrate anion ($NO_3^-$) and an elemental metal to a subject with a headache, such as a migraine, can alleviate their headache pain.

The established school of thought has been that certain foods are migraine triggers due to their high nitrate content, for example, cured meats and wine. It has been thought that the ingested nitrates can be converted into nitric oxide, which, while having beneficial cardiovascular effects, has been known to cause migraines. In fact, there have been many reports that some people develop headaches within minutes to hours after eating foods with nitrites, such as sausages or other cured meats and fish. Additionally, it is well known that organic nitrate medications, such as nitroglycerin and isosorbide dinitrate, which have pharmaceutical effects from the release of nitric oxide, cause headaches, including migraines.

However, as shown in the examples, orally administering an effective amount of a source of nitrate anion ($NO_3^-$) and an effective amount of an elemental metal to a subject suffering from a migraine reduces the subject's migraine symptoms. In some aspects, the method further comprises administering to the subject an effective amount of an acid.

The inorganic nitrate is optimally administered at an amount of 5-3000 mg. In some aspects, the effective amount of inorganic nitrate is 20-2000 mg or 50-1500 mg.

The elemental metal is optimally administered at an amount of 10 to 1000 mg. In some aspects, the effective amount of elemental metal is 50-400 mg. In a particular embodiment, the effective amount of the elemental metal is 200 mg.

The acid is optimally administered at an amount of 10 to 10000 mg. In some aspects, the effective amount of the acid is 100-2000 mg. In a particular embodiment, the effective amount of the acid is 200-1000 mg.

The elemental metal is an alkaline earth metal, an alkali metal, or a transition metal. Because elemental metals are reactive, they are not found in nature. Rather they exist as ores which contain a mixture of various metallic compounds such as salts and oxides. As such, complex extraction and purification utilizing physicochemical methods is required to produce elemental metals. In some embodiments, the elemental metal is elemental magnesium, elemental calcium, elemental lithium, elemental zinc, elemental sodium, elemental potassium, elemental beryllium, elemental rubidium, elemental cesium, elemental aluminum, elemental gallium, elemental indium, elemental tin, elemental bismuth, elemental scandium, elemental titanium, elemental vanadium, elemental chromium, elemental manganese, elemental cobalt, elemental manganese, elemental scandium, elemental titanium, nickel, elemental copper, elemental zinc, elemental yttrium, elemental zirconium, elemental niobium, elemental molybdenum, elemental technetium, elemental ruthenium, elemental rhodium, elemental palladium, elemental silver, elemental cadmium, elemental lanthanum, elemental hafnium, elemental tantalum, elemental tungsten, elemental rhenium, elemental osmium, elemental iridium, elemental platinum, elemental gold, elemental manganese or elemental iron. In some embodiments, the elemental metal is selected from the group consisting of: elemental magnesium, elemental calcium, elemental lithium, elemental zinc, and elemental iron. In some embodiments, the subject is administered a combination of elemental metals.

Thus, in some aspects, the composition administered to the subject comprises more than one elemental metal. The elemental metal may be in any form, for example, a powder or granules. Changing the size and the surface area of the elemental metal may be utilized to affect the reaction rate between the metal and the nitrate and the acid. It has thus been found that smaller particle sizes of the elemental metal result in a more rapid reaction, producing greater amounts of NO in a smaller amount of time.

In some aspects, the source of nitrate anion ($NO_3^-$) is a nitrate salt of an amino acid or amino acid derivative (for example, creatine nitrate, arginine nitrate, carnitine nitrate, n-acetyl carnitine nitrate, citrulline nitrate, betaine nitrate, and proline nitrate), an inorganic nitrate salt (for example, magnesium nitrate, sodium nitrate, potassium nitrate, calcium nitrate, and lithium nitrate, or their mixed salts, co-crystalline formulations, and hydrates), or a natural nitrate source. For natural nitrate sources, the nitrate has been concentrated and/or isolated from a natural source, such as a botanical nitrate source. Examples of natural nitrate sources include, but are not limited to, beet juice, beet juice powder, concentrated beet juice powder, celery powder, spinach and red spinach extract, and *Amaranthus* extract. In preferred implementations, the nitrate content of natural nitrate sources is standardized so as to provide the sufficient amount of nitrate. In some aspects, the composition comprises more than one source of nitrate anion ($NO_3^-$).

In some aspects, the source of nitrite anion ($NO_2^-$) is a nitrite salt of an amino acid or amino acid derivatives (for example, creatine nitrite, arginine nitrite, carnitine nitrite, n-acetyl carnitine nitrite, citrulline nitrite, betaine nitrite, and proline nitrite), an inorganic nitrite salt (for example, magnesium nitrite, sodium nitrite, potassium nitrite, calcium nitrite, and lithium nitrite, or their mixed salts, co-crystalline formulations, and hydrates), or a natural nitrite source. For natural nitrite sources, the nitrite can be concentrated and/or isolated from a natural source, such as a botanical nitrite source.

Also disclosed is a method of preventing the onset of a headache, for example, a migraine, from ingestion of an organic nitrate (such as nitroglycerin or isosorbide dinitrate) or inorganic nitrate (such as a nitrate salt found in cured meats). This method comprises administering an effective amount of an elemental metal with the organic nitrate or inorganic nitrate.

Figure 3:
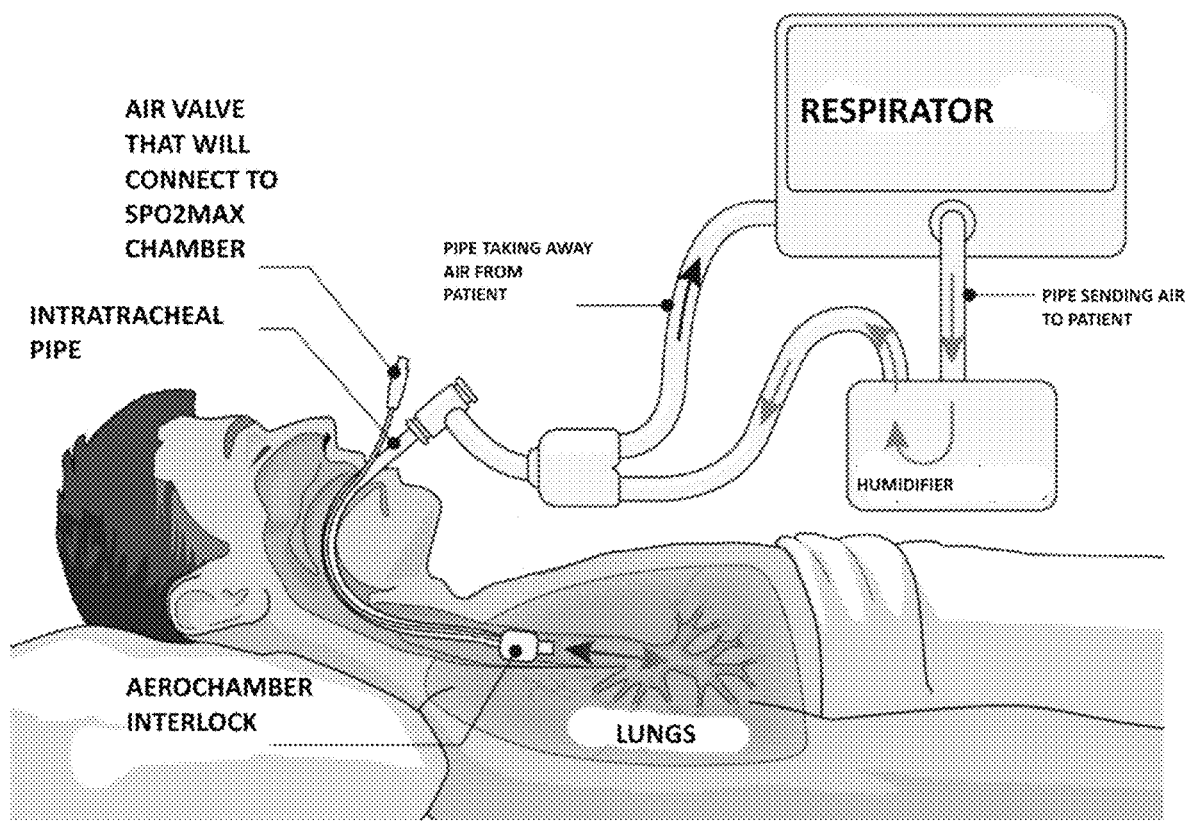
FIG. 3 depicts, in an exemplary implementation, administration of NO and $H_2$ gas to an ICU patient connected to a respirator, wherein the NO and $H_2$ are administered through the air valve inlet, which is typically used to insert nebulized drugs.
Figure 4:
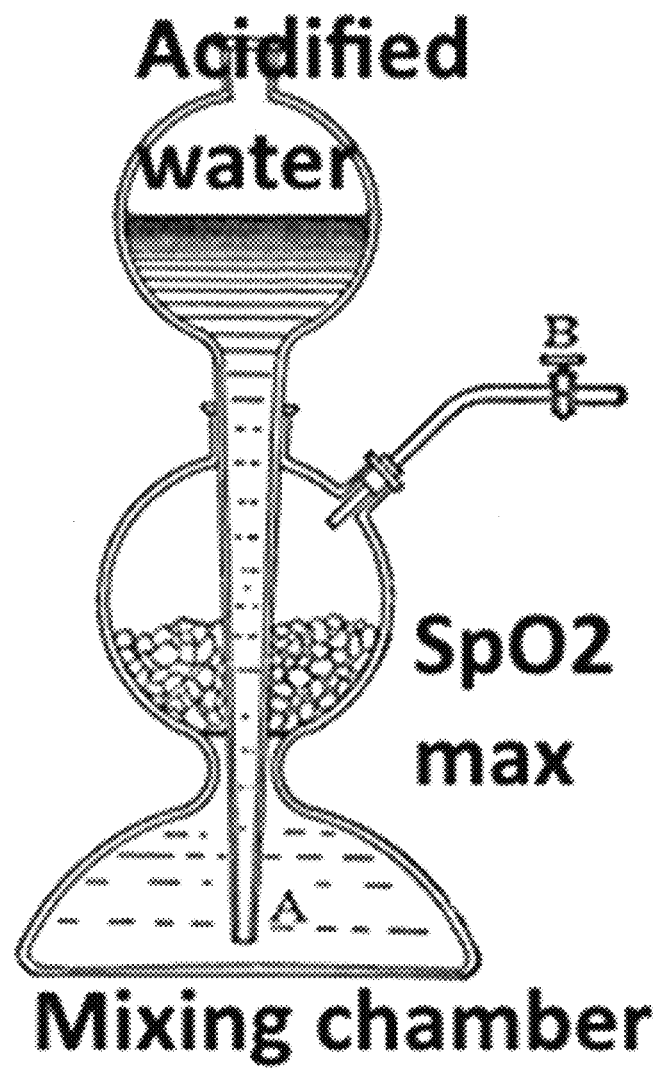
FIG. 4 depicts an exemplary apparatus which can be utilized to cost effectively produce the combination of NO, HNO, and hydrogen gases. The apparatus comprises three compartments, where the top compartment houses a solution of acidified water (preferably acidified with citric acid), the middle compartment houses the SpO2 composition, and the bottom compartment is a mixing chamber, where the acidified water in top compartment would drip into the mixing chamber where it would mix with the SpO2 composition also dropping into the mixing chamber from the middle compartment.

In some embodiments, the elemental metal and nitrate and/or nitrite anion are contained in a system for sustained release of NO. For example, the system may be a time-released system (such as a diffusion system, a dissolution system, an osmotic system, and ion-exchange resin), a floating system, a bio-adhesive system, or a matrix system where exposure to the acid or acid solution is controlled. In other implementations either mechanical or electronic methods may be utilized to release the metal and nitrate into the acid solution in a continuous manner to allow for sustained NO gas release. In a particular implementation, the system for sustained release of NO described herein comprises three compartments in fluid connection (see, for example, FIG. 4). The top compartment houses a solution of acidified water (preferable with citric acid), the middle compartment houses the composition, and the bottom compartment is a mixing chamber, where the acidified water in the top compartment would drip into the mixing chamber mixing with the composition also dropping into the mixing chamber from the middle compartment. The apparatus enables easy adjustment to the amounts of NO, HNO and $H_2$ administered to the patient by controlling the reaction rate of the acidified water and the composition. The reaction rate may be controlled by regulating the acidity of the solution, regulating the drip rate of acidified water, regulating the particle size of the composition, or regulating the heat in the mixing chamber such as with a heating element that has a built-in thermostat (increasing heat increases the reaction's rate). A similar scheme may be utilized to administer $NO/H_2/HNO$ gas in non-ICU patients using a respiratory system, either in home or in a hospital environment, the only difference being that the patient would have to wear a mask or equivalent delivering the gases, instead of an endotracheal tube (see FIG. 3).

Accordingly, a kit for safely administering NO gas to a patient is disclosed herein. The kit comprises a nitrite or a nitrate; an elemental metal, wherein the nitrite and/or the nitrate and the elemental metal are packaged together; an acid; and instructions for combining the nitrite and/or the nitrate, the elemental metal, and the acid to generate NO gas without generating $NO_2$ gas and for administering the generated NO gas to a patient. In some embodiments, the kit further comprises a vessel capable of housing liquid and gas constituents, for example, a water pipe. In some aspects, the nitrite or the nitrate in the kit is a salt, for example, a nitrite salt or a nitrate salt. Exemplary salts include sodium nitrite, potassium nitrite, sodium nitrate, and potassium nitrate. The elemental metal in the kit is selected from the group consisting of: elemental magnesium, elemental calcium, elemental lithium, elemental zinc, elemental sodium, elemental potassium, elemental beryllium, elemental rubidium, elemental cesium, elemental aluminum, elemental gallium, elemental indium, elemental tin, elemental bismuth, elemental scandium, elemental titanium, elemental vanadium, elemental chromium, elemental manganese, elemental cobalt, elemental manganese, elemental scandium, elemental titanium, nickel, elemental copper, elemental zinc, elemental yttrium, elemental zirconium, elemental niobium, elemental molybdenum, elemental technetium, elemental ruthenium, elemental rhodium, elemental palladium, elemental silver, elemental cadmium, elemental lanthanum, elemental hafnium, elemental tantalum, elemental tungsten, elemental rhenium, elemental osmium, elemental iridium, elemental platinum, elemental gold, elemental manganese and elemental iron.

In some implementations, the method comprises providing the acid in powder form and mixing with the nitrate or the nitrite anion and/or the elemental metal before dissolving in a solvent so that NO gas is produced. The acid in powdered form may be, for example, citric acid, malic acid, or fumaric acid. In particular embodiments, the solvent used is water, as it is safe, non-toxic and readily available. However other protic and/or polar solvents could be utilized such as ammonia, ethanol, acetic acid, and the like. The water or solvent need not be pure and other compounds can be dissolved into it as well, such as aromas, scents, other medicine, and the like. In some embodiments, the acid is a salt of a strong acid with a weak base, which when dissolved in water or some other polar and/or protic solvent, results in the formation of an acidic solution. Thus, the acid may be ammonium chloride, ammonium nitrate, or creatine nitrate for example. In certain implementations, where the nitrate anion is provided as a nitrate salt formed with weak bases (such as creatine nitrate or proline nitrate for example), the nitrate salt can serve as the source for both the acid and the nitrate anion.

It will be understood that although the usual sequence of adding the ingredients of the formula is first creating an acid solution and then adding simultaneously the elemental metal and the nitrate, such a sequence is not necessary and there can be variation. For example, the step of combining a nitrate anion and an elemental metal in an acidic solution may comprise simultaneously adding the nitrate, the powdered acid, and the elemental metal in the water, or may comprise preparing a solution of a nitrate in water and then adding the acid and elemental metal. The critical feature of the disclosed methods is that the elemental metal cannot be allowed to fully react with the acid, which forms salts of the elemental metal and not NO gas. Thus, if one was to add elemental magnesium metal in an acid solution and then after the reaction completed (which would be indicated by dissolution of the magnesium in the liquid in its salt form) add a nitrate, no nitric oxide gas would form.

In some aspects, the composition disclosed and used in the methods herein is in the form of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof. The composition may further comprise an acceptable additive and/or an acceptable carrier. The acceptable additive may be selected from at least one member from the group consisting of: a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, and a thickener. The acceptable carrier may be selected from at least one member from the group consisting of: an excipient, a lubricant, a binder, a disintegrator, a diluent, an extender, a solvent, a suspending agent, a dissolution aid, an isotonization agent, a buffering agent, a soothing agent, and an amphipathic lipid delivery system. In some aspects, the composition is in a form suitable for oral administration. In other aspects, the composition is in a form suitable for inhalation of the gases produced when in contact with an acidified solvent.

EXAMPLES

Example 1

An open label case series trial performed by the FSPE Applied Bioenergetics Lab (University of Novi Sad, Lovcenska 16, Novi Sad 21000, Serbia) evaluated the effects of a composition comprising 1200 mg of potassium nitrate, 200 mg of elemental magnesium, 50 mg of elemental zinc administered in one capsule, and 1000 mg of citric acid co-administered in another capsule, on blood oxygen saturation level ($SpO_2$) and patient-reported outcomes in COVID-19 patients.

Five adult patients (3 males and 2 females, 37.0±4.4 years old) with COVID-19 having breathing difficulties and $SpO_2$<95% and free from other pulmonary and cardiovascular conditions were recruited for this study. The participants received the composition every 4 hours during a 48-hour monitoring period. No other treatments for an improvement in oxygen saturation level were administered during the trial. $SpO_2$ and patient-reported outcomes were evaluated at baseline (pre-intervention) and at each 4-hour time point throughout the trial.

$SpO_2$ improved immediately upon administration of the composition for all participants (increase of 1-7%, mean increase 3.6±2.7 points; 95% confidence interval from 0.3 to 7.0). $SpO_2$ remained above baseline values throughout the monitoring interval with values persisting over the threshold value (>92%) for all patients and at each time point during the 48 hours. No patients reported any side effects of the intervention. In addition to the improvements in blood oxygen saturation level, one patient (female, 39 years old) reported a reduction in cough, breathing difficulties, and chest pain. Another patient (male, 38 years old) reported attenuated diarrhea. A third patient (female, 35 years old) reported reduction of fatigue and headache.

Example 2

Five subjects (males, ages 34 to 52 years old) each with a respiratory illness and having $SpO_2$ less than 92% were administered a composition comprising 1200 mg of potassium nitrate, 200 mg of elemental magnesium, 50 mg of elemental zinc in one capsule, co-administered with another capsule containing 1000 mg of citric acid. Their blood oxygen saturation level was measured between 15 to 80 minutes after ingestion of the composition. Their symptoms related to the respiratory illness were also recorded before and after ingestion of the composition. Table 2 summarizes the results.

TABLE 2

Improvement of respiratory symptoms after treatment.

| Subject Age (years) | $SpO_2$ (%) Before | $SpO_2$ (%) After | Symptoms | Alleviated Symptoms |
|---|---|---|---|---|
| 34 | 92 | 98 | Fatigue | Fatigue |
| 46 | 93 | 98 | Headache | Headache |
| 39 | 92 | 97 | Fatigue, cloudy head | Cloudy head |
| 45 | 90 | 95 | Difficulty breathing | Difficulty breathing |
| 52 | 89 | 98 | Body aches, anxiety | Anxiety |

Example 3

1000 mg of citric acid was mixed in a beaker bong containing warm water to produce an acid solution. A prefilled capsule containing 200 mg of elemental magnesium and 1000 mg of potassium nitrate was emptied into the bong containing the acid solution. A 58-year-old male subject suffering from a migraine inhaled the produced gas via the beaker bong. The subject reported that his headache stopped and that he could breathe easier. He also reported his energy and concentration levels increased.

Example 4

A male 58-year-old subject suffering from a migraine ingested a capsule comprising 1000 mg citric acid and a capsule comprising 1200 mg $KNO_3$, 200 mg elemental magnesium, and 50 mg elemental zinc. Within 5 minutes of ingesting both capsules, the subject saw alleviation of migraine symptoms. 30 minutes after ingesting the capsules, the subject reported that the migraine symptoms had disappeared.

Example 5

A 53-year-old female subject that tested positive for COVID-19 complained of having a migraine lasting one month after cessation of the viral infection. She was administered a capsule comprising 1000 mg citric acid and a capsule comprising 1200 mg $KNO_3$, 200 mg elemental magnesium, and 50 mg elemental zinc. She experienced immediate relief of her headache symptoms.

Example 6

A 42-year-old male subject ingested 5 mg (2 capsules) of sustained release nitroglycerin (Supranitrin, GAP. A.E., Greece) and developed a migraine 30 minutes later. The migraine continued for over two hours. After a 3-day washout period, the subject ingested 5 mg (2 capsules) of sustained release nitroglycerin with 200 mg elemental magnesium powder (60-200 mesh size). Although the subject felt lightheaded after ingesting the combination of sustained release nitroglycerin and elemental magnesium, he did not develop a migraine from ingestion of the nitroglycerin.

Example 7

A 42-year-old male subject experiences a migraine upon ingestion of 2.5 mg nitroglycerin. He then ingested 2.5 mg nitroglycerin with 200 mg of elemental magnesium powder (60-200 mesh size). 20 minutes later his migraine had disappeared.

We claim:

1. A method of treating a headache in a subject, the method comprising administering to the subject an effective amount of an elemental metal and an effective amount of a source of nitrate anion, wherein the elemental metal is selected from elemental magnesium, elemental calcium, elemental zinc, or any combination thereof.

2. The method of claim 1, wherein the headache is a migraine.

3. The method of claim 1, wherein the effective amount of the elemental metal is 10-2000 mg.

4. The method of claim 1, where the elemental metal is elemental magnesium.

5. The method of claim 4, wherein the effective amount of the elemental magnesium is 10-1000 mg.

6. The method of claim 4, wherein the effective amount of the elemental magnesium is 50-400 mg.

7. The method of claim 6, wherein the effective amount of the elemental magnesium is 200 mg.

8. The method of claim 4, wherein the elemental magnesium has a mesh size of 60-280.

9. The method of claim 1, wherein the source of nitrate anion is an inorganic nitrate.

10. The method of claim 9, wherein the inorganic nitrate is a nitrate salt.

11. The method of claim 9, wherein the effective amount of the inorganic nitrate is 5-3000 mg.

12. The method of claim 9, wherein the effective amount of the inorganic nitrate is 20-2000 mg.

13. The method of claim 9, where the effective amount of the inorganic nitrate is 50-1500 mg.

14. The method of claim 1, further comprising administering to the subject an effective amount of an acid.

15. The method of claim 14, wherein the acid is selected from the group consisting of: ascorbic acid, tartaric acid, succinic acid, malic acid, and adipic acid.

16. The method of claim 14, wherein the effective amount of the acid is 10-10000 mg.

17. The method of claim 14, wherein the effective amount of the acid 100-2000 mg.

18. The method of claim 14, wherein the effective amount of the acid is 200-1000 mg.

19. A method of preventing a headache caused by ingestion of an organic nitrate and/or an inorganic nitrate, the method comprising: ingesting the organic nitrate and/or the inorganic nitrate with an effective amount of an elemental metal, wherein the elemental metal is selected from elemental magnesium, elemental calcium, elemental zinc, or any combination thereof.

20. The method of claim 19, wherein the organic nitrate is nitroglycerin or isosorbide dinitrate.

21. The method of claim 19, wherein the elemental metal is elemental magnesium.

22. The method of claim 21, wherein the effective amount of the elemental magnesium 10-1000 mg.

23. The method of claim 21, wherein the effective amount of the elemental magnesium is 50-400 mg.

24. The method of claim 21, wherein the effective amount of the elemental magnesium is 200 mg.

25. The method of claim 21, wherein the elemental magnesium has a mesh size of 60-280.

26. The method of claim 19, wherein the effective amount of the elemental metal is 10-2000 mg.

* * * * *